United States Patent [19]

Bellos et al.

[11] Patent Number: 4,671,815

[45] Date of Patent: Jun. 9, 1987

[54] WATER SOLUBLE BIOCIDES

[75] Inventors: Thomas J. Bellos, Kirkwood; Derek Redmore, Webster Groves, both of Mo.

[73] Assignee: Petrolite Corporation, St. Louis, Mo.

[21] Appl. No.: 74,930

[22] Filed: Sep. 13, 1979

Related U.S. Application Data

[63] Continuation-in-part of Ser. No. 600,101, Jul. 29, 1979, abandoned, and a continuation-in-part of Ser. No. 380,202, Jul. 18, 1973, abandoned.

[51] Int. Cl.$^4$ ............................................. A61K 31/26
[52] U.S. Cl. ....................................... 71/67; 260/404; 514/516
[58] Field of Search .................... 424/304, 337; 71/67; 260/404

[56] References Cited

U.S. PATENT DOCUMENTS

| | | |
|---|---|---|
| 1,790,097 | 1/1931 | Kaufmann . |
| 2,541,078 | 2/1951 | Swaney . |
| 2,657,178 | 10/1953 | Robinson . |
| 2,734,028 | 2/1956 | Domogalla . |
| 2,878,155 | 3/1959 | Cruickshank . |
| 2,894,905 | 7/1959 | Bernard . |
| 2,959,517 | 11/1960 | Bowers et al. . |
| 3,051,757 | 8/1962 | Johnston . |
| 3,138,519 | 6/1964 | Riden, Jr. et al. ............... 424/337 |
| 3,231,509 | 1/1966 | Shema . |
| 3,300,375 | 1/1967 | Wehner . |
| 3,426,134 | 2/1969 | Shema ............................ 424/302 |
| 3,443,924 | 5/1969 | Papp et al. ....................... 71/67 |
| 3,591,513 | 7/1971 | Tate ................................. 252/180 |
| 3,674,457 | 7/1972 | Wolfson ........................... 71/67 |
| 3,716,351 | 2/1973 | Kunkel et al. ................... 71/67 |
| 3,792,084 | 2/1974 | Quinlan ........................... 260/502 S |
| 3,905,797 | 9/1975 | Kunkel et al. ................... 71/66 |

FOREIGN PATENT DOCUMENTS

| | | | |
|---|---|---|---|
| 1157883 | 7/1969 | United Kingdom | 424/302 |

OTHER PUBLICATIONS

McCutcheon's–Detergents & Emulsifiers, 1973, pp. 20, 54, 69, North American Ed.

Armour Chem. Div., Armour Chem. and Fatty Acids, Armeens, Ethomeens, Ethomids and Ethofats, 1967 or earlier.

Schwartz et al., Surface Active Agents, vol. 1 (1949 ed.), pp. 308 & 512.

*Primary Examiner*—Frederick E. Waddell
*Attorney, Agent, or Firm*—Sidney B. Ring; Leon Zitver

[57] ABSTRACT

This invention relates to salts of oxyalkylated amino compounds which render normally water insoluble components such as biocides, soluble in water and thereby improving their usefulness and effectiveness. These amino compounds render biocides such as methylene bis(thiocyanate) (MBT) and/or bis(trichloromethyl) sulfone (BTMS) water soluble. The soluble forms of these biocides afford more predictable, consistent and effective biocidal results when applied to systems contaminated with microorganisms such as bacteria, fungi, algae, molds, and certain yeasts and thus offer considerable advantages over insoluble, dispersible, emulsified forms of these biocides.

6 Claims, No Drawings

WATER SOLUBLE BIOCIDES

This application is a continuation-in-part of Ser. No. 600,101 filed July 29, 1976 now abandoned, and Ser. No. 380,202 filed July 18, 1973, now abandoned.

This invention relates to water soluble biocides useful in the control of microorganisms such as bacteria, algae, mold, fungi, yeast and bacteria associated slime. Manufacturing as well as production processes use huge quantities of raw as well as potable water that must be treated with biocides in order to assure product and production standards. Typically, cooling towers, paper pulp mills, canning industries, animal hide processing plants, secondary oil recovery using water flooding, industrial water systems, to name a few, require the use and recycling of the water used in these processes. These systems become easily contaminated with microorganisms such as bacteria, algae, fungi, yeast, etc., due to exposure to contaminants encountered in the process of manufacturing and/or from the products being processed. These waters become a breeding media for microorganisms which must be controlled and/or eliminated. Biocides have been developed which control such contaminants which, if left unchecked, will destroy equipment and/or reduce the quality of a manufactured product, i.e., paper and leather products.

Two biocides employed to control bacteria, mold, fungi and algae are methylene bis(thiocyanate) and bis(trichloromethyl)sulfone. These products, singly or in combination with each other, control most bacteria, algae, mold, fungi and yeast common to the paper and hide processing industries as well as the bacteria, algae, yeast and mold contaminants associated with cooling towers, industrial water processing systems, water flooding, water sources, disposal wells, etc., if they are properly formulated. Both of these products which are substantially insoluble in water have been used for years by industry separately and/or in combination with each other. MBT is 0.5% soluble and BTMS essentially insoluble in water at room temperature.

These products singly and/or mixed are sold as dilutions in such solvents as N,N-dimethyl formamide 2-propanol, acetone, acetonitrile, various dispersing agents/solvent combinations as well as in emulsifying agent to keep these insoluble agents dispersed and/or suspended in water. The dispersions and emulsions of these products when pumped continuously through systems which are subjected to changing temperatures and on/off operation tend to break and precipitate. An emulsion or a dispersion of these chemicals at best gives "short lived" protection from bacteria, mold, fungi, algae and yeast as they are required to make physical contact with these contaminants which they cannot do if precipitated. It is therefore a great advantage if these products could be rendered water soluble thereby rendering the biocides uniformly dispersed or homogeneous throughout the entire system.

This invention relates to methods and chemical agents as illustrated by salts of oxyalkylated amines that render bis(trichloromethyl)sulfone and/or methylene bis(thiocyanate) soluble in water. These products are true solutions which do not require agitation to keep them dispersed in water.

It has been further discovered that, although the active ingredients, namely bis(trichloromethyl)sulfone and/or methylene bis(thiocyanate) are degraded when oxyalkylated amines in non-salt form are employed, the salt form of oxyalkylated amines, particularly as the hydrohalide and most particularly as the completely neutralized oxyalkylated amine, forms a true solution in which the active ingredients are stable.

It has been further discovered that the active ingredients are most stable in those systems where the presence of water is minimized. Therefore, the presence of water in the oxyalkylated amines salts and resulting solutions of this invention is minimized. In practice, water is present in concentration of less than about 1.5% by weight, such as less than about 1.25%, for example less than about 1%, but preferably less than about 0.75%.

The biocides themselves are described in U.S. Pat. No. 2,959,517; 2,252,855 and 3,426,134. These biocides are dispersed or emulsified in water. These emulsions or dispersions break readily and rapidly and most of the biocide contained therein, after precipitation at pH's typical of systems in which they are used, are not "true solutions" unaffected by filtration or ultracentrifugation.

In constrast, since the products of this invention are not dispersed and emulsified products, they are unaffected by these actions. For example when 1% solutions of our biocidal products are filtered through 1 (micron) filter paper (VCW P04700 Millipore) and the filtered solution is tested for biocidal effectiveness, the filtered solution is as biocidally active as the unfiltered solution. Likewise when a 1% solution of the biocidal products of this invention were subjected to a force equal to 49,000 G in an ultracentrifuge, the biocidal activity of the solutions remains unchanged.

In contrast when 1% solutions of the corresponding prior art commercially available products, formulated in "dispersing agents," are filtered, the filtered solution is less effective than the unfiltered solutions. In addition, the same prior art products, when centrifuged, separate into two layers, the aqueous layer exhibiting less biocidal activity than the uncentrifuged product. Solids centrifuged from the 1% solutions of these commercial products contained surfactant which is the dispersing agent, bis(trichloromethyl)sulfone, or methylene bis(thiocyanate) and a hydrocarbon product. The aqueous layer contained portions of all of the products found in the solid layer but at a greatly reduced level. The biocidal effectiveness of the aqueous layer exhibited less control over the aerobic bacteria used in our screening tests. Most tests for biocidal agents suggest the use of test methods centered around "dynamic" procedures which keep the bacteria in a growth media and the biocide being evaluated under constant agitation. These methods disperse the insoluble biocides as well as dispersible products, thereby maintaining their distribution throughout the bacteria growth media. Therefore, many biocides which, under static conditions precipitate and test poorly as bacterial growth control agents, actually exhibit better test results with agitation than produced under actual field or use conditions.

In contrast, the products of this invention are so superior to the commercial forms of methylene bis(thiocyanate) and/or bis(trichloromethyl)sulfone that their "unique" properties and the advantages of using soluble forms of these chemicals outweighs and precludes the use of any other form of these products.

To further test the uniqueness of our soluble biocidal forms, we prepared 20% solutions of $CaCl_2$, NaCl and added the products of the invention to these solutions at a level of 1% and found they were completely soluble whereas the prior art commercial "dispersible" forms were insoluble in these solutions, and had to be kept agitated to maintain their distribution throughout these brines. Waters of various pH typical of locations where these products might be used were prepared. The soluble products of this invention were unaffected by these pH changes. Field studies at actual water tower locations in various parts of the United States were conducted and the biocidal effects of our soluble products were not noticeably affected by the normal range of pH encountered in typical operations such as in cooling tower, paper pulp, leather processing, etc., applications.

Thus, we have discovered that compounds, which are normally insoluble in water, can be rendered water soluble by forming complexes thereof by combining with solubilizing agents.

The complexes of this invention are illustrated by compounds which are capable of forming complexes by combining with solubilizing agents, such as salts of oxyalkylated amines so that the resulting complex is water soluble. This is in contrast to the same insoluble compounds which are rendered dispersible in water by forming aqueous emulsions of non-aqueous solutions of such water insoluble compounds. In the present invention the complexes are true solutions. They are not emulsions or merely soluble in a solvent carrier.

By means of the present invention complexes are formed from these water insoluble compounds by means of the complexing agents of this invention to yield water soluble complexes ideally represented as A.B, where A is the water insoluble compound and B is the complexing agent.

Although the method by which they combine is not known, the complexes formed are water soluble. Stated another way the novel complexes formed are directly soluble in water in contrast to the prior art where they must be emulsified in order to be effectively employed in aqueous systems.

The complexing agents of this invention are salts of oxyalkylated amines.

Any oxyalkylatable mono-, poly-, cyclic-, heterocyclic-, etc., amine can be oxyalkylated according to this invention to place $(OA)_n$ units herein, where OA represents the alkylene oxide derived radical of a unit where n can be, for example 1–100 or more, such a 1–50, for example 1–20, but preferably 1–10.

Oxyalkylated amines may be represented by the formula

where  represents the amine moiety which originally contained at least one oxyalkylatable group (monoamines, polyamines, heterocyclic amines, etc.) and $(OA)_n$ has the meaning stated above. Oxyalkylation may take place at one or more positions determined by the number of oxyalkylatable positions.

Thus, any of the oxyalkylatable amines disclosed herein and elsewhere can be oxyalkylated and employed in this invention.

$(OA)_n$ is derived from any suitable $\alpha,\beta$ alkylene oxide, for example, alkylene oxides of the formula

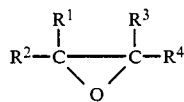

where $R^1$, $R^2$, $R^3$, $R^4$ are hydrogen or a substituted group, for example alkyl, cycloalkyl, aryl, etc., for example ethylene oxide, propylene oxide, butylene oxide, amylene oxide, octylene oxide, styrene oxide, methylstyrene oxide, cyclohexene oxide (where $R^1$ and $R^3$ are joined to form a ring), etc.

Equivalents of alkylene oxides can also be employed, for example alkylene carbonates, i.e., ethylene carbonate, propylene carbonate, butylene carbonate, etc. In addition alkylene oxides of the glycide, methyl glycide, etc., type and their equivalents can also be employed. $(OA)_n$ denotes (1) homo units for example, $-(OEt)_n-$, $-(OPr)_n-$, $-(OBu)_n-$, $-(O\text{ Octyl})_n-$,

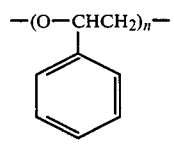

etc., (2) block units, $-(OEt)_a(OPr)_b-$, $-(OEt)_a(OBu)_b-$, $(OPr)_a(OEt)_b(OPr)_c$, $(OEt)_a(OPr)_b(OBu)_c$,

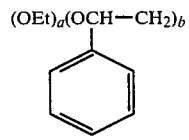

etc., where $a+b+c=n$;

(3) hetero units containing group which are random mixtures of more than one oxide $(OEt-OPr)_n$, $(OPr-OBu)_n$, wherein the ratio of each oxide to the other is for example 1–99 to 99–1;

(4) hetero-homo units for example, $(EtO)_a(EtO-PrO)_b$, $(EtO)_a(PrO)_b(EtO-PrO)_c$, $(EtO-PrO)_a(BuO)_b$ etc.

The following are representative examples of amines which can be oxyalkylated to form the complexing agents of this invention:

1. $R-NH_2$, where R has about 1 to 22 carbons such as aliphatic, alkaryl, etc. Specifically $C_{18}H_{35}NH_2$ (ARMAK'S ARMEEN T).
2. $H_2NCH_2CH_2OH$, monoethanolamine.
3. $H_2NCH_2CH_2NH_2$, ethylenediamine.
4. Polyamines such as diethylenetriamine, etc.
5. Amides with amine tails

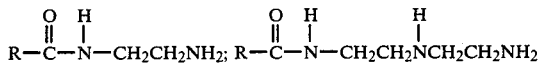

where R has about 1–22 carbons but preferably about 10–18 carbons and most preferably alkyl.

6. Any amine capable of being modified with alkylene oxide either singly or a combination of alkylene oxides, i.e., ethylene and propylene oxide, in any order of addition where the end product has sufficient oxide so as to render it water soluble. These products will function more or less to solubilize particular insoluble compounds and render them soluble without loss of their intrinsic properties, i.e., complexing agent+insoluble biocide equals water soluble biocide. In fact, in many instances intrinsic properties are enhanced because of more effective contact in solution.

The following are non-limiting examples of amines that can be oxyalkylated to yield complexing agents of this invention:

I. MONOAMINES

A. Primary monoamines

These include compounds of the formula R—NH$_2$, where R is a substituted group preferably a hydrocarbon group, for example alkyl, cycloalkyl, aryl, alkenyl, heterocyclic, substituted derivatives of the above, etc.

ALKYL

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, eicosyl, docosyl, etc., having 1–50 or more carbons, such as 1–30, but preferably 1–18 carbons.

The term "alkyl" also includes isomers of the straight chain group wherein branching occurs along the chain, for example

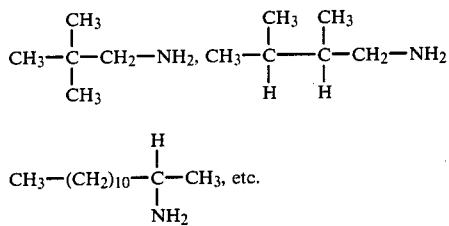

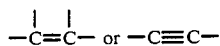

ALKENYL AND ALKINYL

These include unsaturated analogues of alkyl groups containing one or more $$-\overset{|}{C}=\overset{|}{C}- \text{ or } -C\equiv C-$$

groups, for example decenyl, dodecenyl, tridecenyl, tetradecenyl, pentadecnyl, hexadecyl, heptadecenyl, octadecenyl, etc., dienes for example octadienyl, etc., trienes, for example octatrienyl, etc., alkinyl, for example butinyl, etc.

CYCLOALKYL

These include

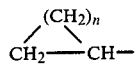

for example cyclobutyl, cyclopentyl, cyclohexyl, cycloheptyl, cyclooctyl, etc.; substituted derivatives thereof, for example alkyl or polyalkyl, for example alkyl cyclohexyl, dialkyl cyclohexyl, etc.

ARYL

These include phenyl, substituted phenyl, alkyl phenyl, polyalkylphenyl, chlorophenyl, alkoxyphenyl, etc., naphthyl, alkyl naphthyl, etc.; benzyl, substituted benzyl, etc. groups.

HETEROCYCLIC

These include furyl, hydrogenated furyl, etc. groups.

B. Secondary amines

These include amines of the formula

where R and R', which may or may not be the same, have the same meaning as stated above, for example dimethyl amine, diethyl amine, dipropyl amine, diamylamine, dihexyl amine, dioctyl amine, didodecyl amine, dihexyldecyl amine, etc., methyl ethyl amine, methyl octyl amine, butyl octylamine, methyl octadecyl amine, etc.; methyl octadecenyl amine, dioctadecenyl amine, etc.; dicyclohexyl amine, methyl cyclohexyl amine, etc.; methyl furyl amine, methyl benzyl amine.

C. Commercial amines

Representative commercial amines are available, for example, these shown in the following tables.

The nomenclature of these amines is derived from either their chain length or source of raw material, for example, Armeen 8D-octyl amine
Armeen C-coconut oil amine
Armeen S-soybean oil amine
Armeen T-tallow amine
Armeen O-oleyl amine
Armeen HT-hydrogenated tallow amine.

Products with "D" designate distilled grade. Products without "D" designate technical grade.

Other commercial amines include the following:

"Primene" amines

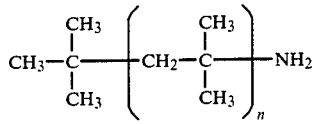

Rosin Amine D

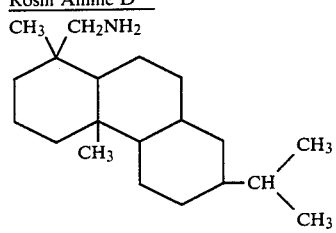

E. Cyclic secondary amines

Also included within the definition of secondary amines are those amines where two of the R groups are joined in a cyclic structure as

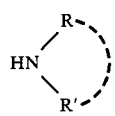

Examples of these amines include piperidine, piperazine, morpholine, etc.

II. POLYAMINES

These include polyamines corresponding to the formula

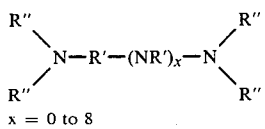

x = 0 to 8 in which R'' (which may or may not be the same) is hydrogen, alkyl, cycloalkyl, aryl, or aralkyl and R' is a divalent radical such as —CH$_2$CH$_2$—, —CH$_2$CH$_2$CH$_2$—,

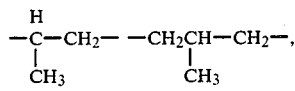

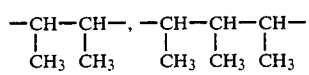

etc.
Ethylenediamine
Diethylenetriamine
Triethylenetetramine
Tetraethylenepentamine
Propylenediamine
Dipropylenetriamine
Tripropylenetetramine
  Butylenediamine
  Aminoethylpropylenediamine
  Aminoethylbutylenediamine

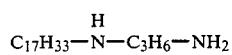

Other polyamines in which the nitrogen atoms are separated by a carbon atom chain having 4 or more carbon atoms include the following: Tetramethylenediamine, pentamethylenediamine, hexamethylenediamine, etc.

Another class of polymaines which may be employed are those sold under the trademark "Duomeen" which is a designation for certain diamines. "Duomeen" amines have the following general formula:

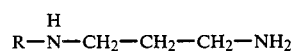

R is an alkyl group derived from a fatty acid or from the mixed fatty acids as obtained from certain oils. The specific "Duomeen" and the source of the radical R are as follows:
(1) "Duomeen" 12, R=lauric
(2) "Duomeen" C, R=coconut oil fatty acid
(3) Similarly, a comparable diamine, obtained from Rosin Amine D and acrylonitrile, can be prepared.

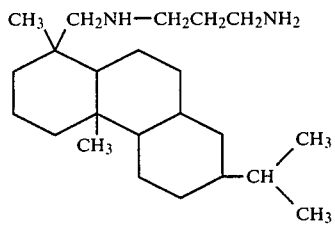

Additional examples of polyamines include the following:

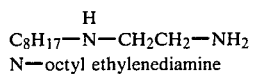
N—octyl ethylenediamine

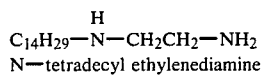
N—tetradecyl ethylenediamine

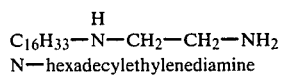
N—hexadecylethylenediamine

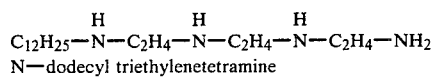
N—dodecyl triethylenetetramine

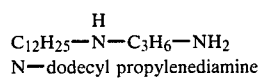
N—dodecyl propylenediamine

Diamines containing tertiary amino groups for example

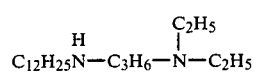

It is to be noted that the above examples show high molal groups, i.e., 8 carbon atoms or more. The same derivatives in which methyl, ethyl, propyl, butyl, amyl, hexyl groups, or the like, appear instead of octyl, decyl, etc., are equally satisfactory.

Acylated polyamines can also be employed provided they are sufficiently basic to form salts, for example:

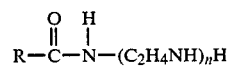

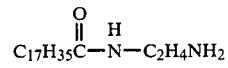

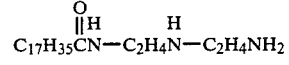

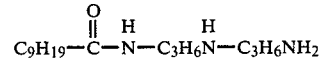

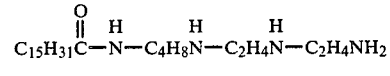

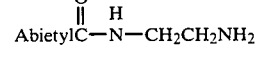

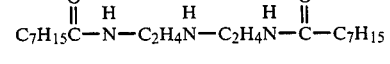

-continued

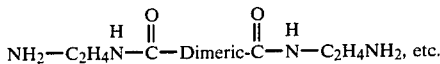
NH$_2$—C$_2$H$_4$N—C—Dimeric-C—N—C$_2$H$_4$NH$_2$, etc.

The particular alkylene oxide or oxides employed, the amounts thereof, the ratios of oxides inter se, will vary widely depending on various factors, for example, the particular amine employed, the particular compound one desires to solubilize, etc. In general, sufficient oxides and types thereof are employed in ratios so that the oxyalkylated amine in combination with the insoluble compound is water soluble.

EXAMPLES

1. Tallow amine Armak Armeen T (C$_{18}$H$_{35}$NH$_2$) with a combining weight of 275/mole is reacted with 15–25, but preferably 22–23, moles of ethylene oxide.
2. Armak Armeen T (C$_{18}$H$_{35}$NH$_2$) with a combining weight of 275/mole is reacted with 15 moles of ethylene oxide.
3. Armak Armeen T (C$_{18}$H$_{35}$NH$_2$) with a combining weight of 275/mole is reacted with 18 moles of ethylene oxide.
4. Monoethanolamine 1 mole is reacted with EtO 2.4 moles and PrO 2.5 moles.
5. Ethylenediamine 1 mole is reacted with EtO 3 moles and PrO 4 moles. 6. Triethylene Tetramine 1 mole is reacted with 6 moles EtO and 6 moles PrO.

The following structures are typical of those utilized in this invention and are presented for purposes of illustration and not of limitation. Salts of these structures are employed.

STRUCTURE I

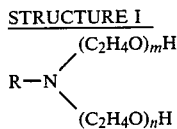

where R equals a linear or branched alkyl group having about 6–22 carbons but preferably about 8–18 carbons, where m+n equals about 3–40 moles of ethylene oxide but preferably about 15–35 moles of ethylene oxide. A typical example of Structure I is one mole of Tallow amine Armeen T. (Armak Chemicals) catalyzed with BF$_3$ etherate to which was added 22 moles of ethylene oxide (Ex. A).

STRUCTURE II
1. NH$_2$CH$_2$CH$_2$OH

2. NH$_2$CH$_2$CH$_2$NH$_2$

3. NH$_2$—C$_2$H$_4$N—C$_2$H$_4$—NH$_2$
    |
    H

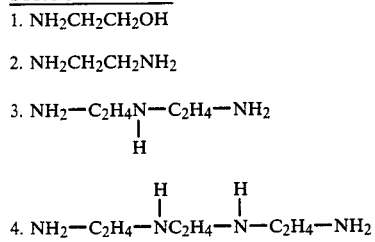
4. NH$_2$—C$_2$H$_4$—NC$_2$H$_4$—N—C$_2$H$_4$—NH$_2$ where the above structures are oxyalkylated with from about 1–50 moles of ethylene oxide, then oxyalkylated with propylene or butylene oxide in the mole range of from about 1–20 moles. For example, one mole of Structure II 3 was oxyalkylated with 3.25 moles of ethylene oxide, then oxyalkylated with 9.5 moles of propylene oxide (Example B.).

STRUCTURE III

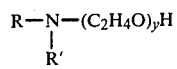  Example (1)

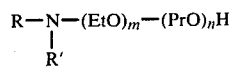  Example (2)

where R and R' in examples 1 and 2 in Structure III are aliphatic groups, linear or branched, saturated or unsaturated, for example having from about 1–18 carbons, or an aromatic group; such as a benzyl or an alkaryl group, for example a dodecylbenzyl group or any combination of the above. Where y in Example (1) is ethylene oxide with a mole range of from about 10 moles to 45 moles, but preferably about 10–38 moles.

Where m in example (2) in Structure III is from about 4 moles to 45 moles, preferably about 5–32 and n is from about 2–35 but preferably about 4 moles to 25 moles.

In some instances, it has been found that mixtures of Structure I and one (or more) of the moieties from Structures II (composite) or Structures III examples 1 and 2 are better than an individual compound. That is, in some instances, mixtures of these complexing agents are better than individual agents.

The following examples are presented for purposes of illustration and not of limitation.

EXAMPLE A

A complexing agent is made by oxyalkylating Armeen T with 22 moles of ethylene oxide $$RN[(EtO)_{11}H]_2$$

in which R is tallow derived.

The complexing agent of Example A in the form of an HCl salt is employed with water-insoluble compounds such as biocides, herbicides, algacides.

EXAMPLE B

Diethylene triamine is oxyalkylated without a catalyst first with 3.25 mole of ethylene oxide and then with 9.5 moles of propylene oxide. This compound in the form of an HCl salt is used as a complexing agent.

Thus the compositions of this invention are salts of the above oxyalkylated amines.

The amino agent employed in this invention will be illustrated by a salt of an amine containing at least one oxyalkylated group and at least one fatty group. It will be illustrated with monoamines.

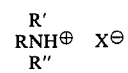

where X is an anion such as those derived from mineral acids but preferably a halogen and most preferably chlorine; where at least one of the R's in the formula is a fatty group, i.e., containing at least about 8 carbons, such as 8–30 carbons, for example 10–25 carbons, but preferably about 12–18 carbons. At least one of the other R groups is an oxyalkylated group. The remaining R groups may be a wide variety of radicals.

The following are representative examples:

$$\begin{array}{c} R' \\ | \\ RNH^\oplus \quad X^\ominus \\ | \\ R'' \end{array}$$

| Ex. | R | R' | R'' | X |
|---|---|---|---|---|
| 1 | $C_{18}H_{35}$ | $CH_3$ | $(CH_2CH_2O)_xH$ | Cl |
| 2 | $C_{18}H_{35}$ | $(CH_2CH_2O)_xH$ | $(CH_2CH_2O)_yH$ | Cl |
| 3 | $C_{12}H_{25}$ | $(CH_2CH_2O)_xH$ | $CH_3$ | $SO_4H$ |
| 4 | ⟨⟩$CH_2$— | $(CH_2CH_2O)_xH$ | $CH_3$ | Cl |
| 5 | R-⟨⟩$CH_2$— | $(CH_2CH_2O)_xH$ | $CH_3$ | Cl |

$x + y$ = about 15–35, optimum

A wide variety of salts can be employed of which the above are illustrative. To more fully understand their effectiveness the results of our biocidal test results were examined. The following method was used to comparatively evaluate our "soluble products," using the agents of the invention against "dispersible forms" or emulsified forms of the bactericides.

DYNAMIC AEROBIC SCREEN TEST

The system was designed to closely resemble actual cooling tower conditions (i.e., aeration, agitation, slightly supportive growth medium). The test procedure is designed to permit both optical and actual cell count evaluation of chemical influence on the test organisms. Both pure and mixed culture evaluation studies are possible.

PROCEDURE

1. A series of milk dilution bottles were prepared containing sterilized 99.0 ml of a slightly supportive growth medium (0.25 gm/L Difco Nutrient Broth in tap water). The test compound was added using a microliter syringe (1.0=10 ppm) graduated in-system dosage level ranging between: 0 or 10, 20,—100 mg/L.

2. An inoculum of 1.0 ml (twice washed by centrifugation in $K_2HPO_4$ buffer) of the test organisms were added to each test chamber to produce an average cell density of 2.5 million colonies/ml (verified by Standard Plate Count Procedure).

3. The test system was exposed to the test bactericide and selected organisms for a period of 72 hours on a shaker (30 cycles/min) at 25° C.

4. Following exposure periods of 24, 48, 72 hours 1.0 ml aliquots were removed from each plate test system onto (Difco) Tryptone Glucose Extract Agar in duplicate. These plates were cultured for 24 hours at 37° C. and read-out.

5. Interpretation of Results: End-points of bactericidal control were read-out on plates showing 100% control of growth.

TEST ORGANISMS AND PROCEDURES USED

Source and Description of Test Organism(s).

*Bacillus cereus* subsp. *mycoides* (ATCC# 14579) aerobic to facultatively anaerobic—Gram-positive. motile rods 1.0 to 1.2 by 3.0 to 5.0 microns. Abundant growth on glucose agar slants. Produces rapid peptonization of milk. Characterized by radial filamentous structures on nutrient agar and flat surfaces (cooling tower fill).

Typical Habitat: Widely distributed in soil, dust, and on plant surfaces.

*Enterobacter aerogenes* (ATCC# 13048)—formerly termed *Aerobacter aerogenes;* Aerobic, to facultatively anaerobic, Gram-negative, non-motile small rods. Ferment glucose and lactose with production of acid and gas. Frequently encapsulated, MRVP-positive, catalase positive. Known to produce large quantities of slime (mucopolyacchloride).

Typical Habitat: Widely distributed in nature, normally found in soil, water, and in intestinal canals of man and animals.

*Pseudomonas aeruginosa* (ATCC# 15442) U.S.D.A. PRD-10 Aerobic to facultatively anaerobic, Gram-negative, motile rods (0.5 to 0.6 by 1.5 microns). Produces rapid liquification of gelatin. Produces large spending grayish-green colonies on agar plates. Nitrates produced from nitrites and nitrogen, Gluclose, lactose, sucrose, maltose not fermented.

Organism known to possess broad spectrum of resistance to various commercial germicides as recorded by: Disinfectant Testing Official Methods of Analysis of Assoc. Office Agriculture. Chem. 10th ed., 1965. J.A.O-.A.C. 52(2): 280–281 (1969).

Typical Habitat: Widely found in soil, polluted water and sewage.

Mixed Culture aerobic bacteria—combined isolates from soil, industrial cooling tower, Mississippi River, and the Kirkwood Municipal Sewage Treating Plant. Composite recognized as quite viable and moderately resistant to typically used quaternary ammonium type bactericides, culture viability capable of producing 3.6–4.2 million colonies/ml in (Difco) Nutrient Broth in 24 hr/37° C. using the Standard Plant Count Procedure.

The following formulations were tested according to the Dynamic Aerobic Screen Test with results showing the superiority of the present invention.

| Formulation | | Composition |
|---|---|---|
| Formula 1 | | |
| A commercial dispersible formula | 50% | MBT |
| | 50% | of a mixture of N,N—dimethyl formamide and Ethylene glycol (dispersible in water) |
| Formula 2 | | |
| water soluble | 15% | MBT |
| | 85% | agent of invention (soluble in water) the hydrochloride salt of Armeen T plus 22 moles EtO |
| Formula 3 | | |
| water soluble | 11.8% | MBT |
| | 88.2% | agent of invention (soluble in water) the hydrochloride salt of Armeen T plus 22 moles EtO |
| Formula 4 | | |
| water soluble | 13% | Bis(trichloromethyl) sulfone |
| | 5% | Methylene bis(thicyanate) |
| | 82% | Agent of invention the hydrochloride of Armeen T plus 22 moles EtO |

-continued

| Armeen T is Tallow - $C_{18}H_{35}NH_2$ | | | | | | |
|---|---|---|---|---|---|---|
| | Result % Kill/Concentration ppm | | | | | |
| Compound | 2.5 | 5.0 | 10 | 25 | 50 | Time |
| Formula 1 | 0 | 60 | 80 | 95 | 95 | 24 hrs. |
| (commercial) | 0 | 0 | 90 | 95 | 99 | 48 hrs. |
| | 0 | 0 | 60 | 95 | 100 | 72 hrs. |
| Formula 2 | 99 | 99 | 100 | 100 | 100 | 24 hrs. |
| (present | 85 | 99 | 100 | 100 | 100 | 48 hrs. |
| invention) | 0 | 99 | 99 | 100 | 100 | 72 hrs. |
| Formula 3 | 77 | 92 | 94 | 99.99 | 100 | 24 hrs. |
| (present | 0 | 80 | 90 | 100 | 99 | 48 hrs. |
| invention) | 0 | 76 | 100 | 100 | 100 | 72 hrs. |
| Formula 4 | 65 | 97 | 100 | 100 | 100 | 24 hrs. |
| (present | 0 | 0 | 90 | 100 | 100 | 48 hrs. |
| invention) | 0 | 0 | 30 | 100 | 100 | 72 hrs. |

While specific examples of the invention have been set forth herein, it is not intended to limit the invention solely thereto but to include all variations and modifications falling within the scope of this invention.

In summary, it has been discovered that salts of the solubilizing agents are more effective in complexing with the insoluble compound than the non-salt form of the solubilizing agent. Whereas the copending application of Thomas J. Bellos, Ser. No. 74,929, filed Sept. 13, 1979, which is a continuation-in-part of Ser. No. 380,202 filed July 18, 1973, now abandoned forms salts in situ, in the present invention the salts are preformed. In general, the salts are prepared by adding about a stoichiometric amount of acid to the amine solubilizer for example according to the following equation:

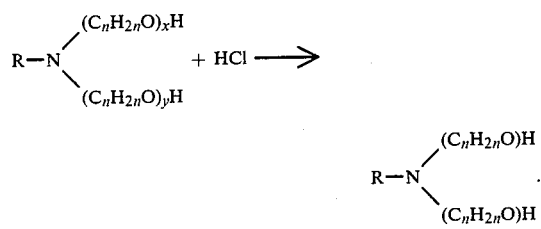

which complexes with the insoluble compound to form a soluble complex.

In certain systems the preformed salt process has certain advantages. For example, where the insoluble compound is sensitive to base, preforming the salt reduces this sensitivity. For example, although methylene bisisothiocyanate (MBT) degrades in the presence of base, it is more stable in acid systems. Since neutralized amine salts are formed by adjusting to a pH on the acid side, (equivalence point pH of about 3.5 to b 4), MBT is more stable in such a system. In addition to enhancing MBT stability, the amine salt synergistically enhances the effectiveness of MBT as a biocide as compared to the MBT amine combination itself.

The following Examples are presented to further illustrate this invention:

TABLE 1

| Ex. | Composition |
|---|---|
| A | Coco amine 1 wt plus 2.5 wts. EtO (amine) |
| B | Coco amine 1 wt plus 2.5 wts. EtO hydrochloride (amine.HCl) |
| C | 15 g amine plus 4 g Sulfone; No heating |
| D | 15 g amine.HCl plus 4 g Sulfone; No heating |
| E | 15 g amine plus 1 g MBT; No heating |
| F | 15 g amine.HCl plus 1 g MBT; No heating |
| G | 15 g amine plus 4 g Sulfone plus 1 g MBT; no heating except for spontaneous exotherm |
| H | 15 g amine.HCl plus 4 g Sulfone plus 1 g MBT; No heating |
| I | 15 g amine plus 4 g Sulfone plus 1 g MBT; 6 hrs @ 89° C. |
| J | 15 g amine.HCl plus 4 g Sulfone plus 1 g MBT; 6 hrs @ 89° C. |
| | Sulfone = bis(trichloromethyl)sulfone |
| | MBT = methylene bis(thiocyanate) |

| 3 Day Dynamic Aerobic Screen Test (According to the procedure of p. 21-24 of this application) | | | | | | | |
|---|---|---|---|---|---|---|---|
| | Percent Kill | | | | | | |
| Ex. | 2.5 | 5 | 10 | 25 | 50 | 100 | (ppm) |
| A | 0 | 0 | 0 | 0 | 0 | 0 | 24 hrs. |
| B | 0 | 0 | 0 | 0 | 0 | 0 | 24 hrs. |
| C | 0 | 0 | 0 | 0 | 30 | 90 | 24 hrs. |
| | 0 | 0 | 0 | 0 | 0 | 0 | 48 hrs. |
| D | 0 | 0 | 0 | 0 | 80 | 90 | 24 hrs. |
| | 0 | 0 | 0 | 0 | 0 | 0 | 48 hrs. |
| E | 0 | 0 | 0 | 0 | 0 | 0 | 24 hrs. |
| F | 0 | 0 | 98 | 100 | 98 | 99 | 24 hrs. |
| | 0 | 0 | 0 | 100 | 95 | 99 | 48 hrs. |
| | 0 | 0 | 0 | 98 | 100 | 98 | 72 hrs. |
| G | 0 | 0 | 98 | 100 | 100 | 100 | 24 hrs. |
| | 0 | 0 | 0 | 100 | 100 | 100 | 48 hrs. |
| | 0 | 0 | 0 | 100 | 100 | 100 | 72 hrs. |
| H | 0 | 99 | 100 | 100 | 100 | 100 | 24 hrs. |
| | 0 | 0 | 98 | 100 | 100 | 100 | 48 hrs. |
| | 0 | 0 | 30 | 100 | 100 | 100 | 72 hrs. |
| I | 0 | 99 | 0 | 100 | 100 | 100 | 24 hrs. |
| | 0 | 0 | 0 | 100 | 100 | 100 | 48 hrs. |
| | 0 | 0 | 0 | 100 | 100 | 100 | 72 hrs. |
| J | 0 | 97 | 100 | 100 | 100 | 100 | 24 hrs. |
| | 0 | 0 | 98 | 100 | 100 | 100 | 48 hrs. |
| | 0 | 0 | 30 | 100 | 100 | 100 | 72 hrs. |

The above table illustrates the following:

(1) The reaction products of the oxyalkylated amine and the sulfone when combined with MBT are excellent biocides (2) The preformed salts of the oxyalkylated amine and the sulfone when combined with MBT are excellent biocides (3) The preformed salts as formed in (2) are superior to those as formed in (1)

(4) The salts of the oxyalkylated amines and MBT are effective biocides.

In addition it is also desirable to minimize the presence of water in the oxyalkylated amine salts and resulting solutions of this invention. In practice water is present in low concentrations for example of less than about 1.5% by weight, such as less than about 1.25%, for example less than about 1%, but preferably less than 0.75%, with an optimum of less than 0.50%. Thus, in practice as close as feasible to anhydrous conditions is employed and any water present is removed by distillation such as by azeotroping, the use of gaseous HCl, etc.

We claim:

1. A water soluble biocidal complex of methylene bis(thiocyanate) and bis(trichloromethyl)sulfone with an oxyalkylated fatty amine salt of the formula

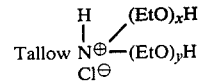

where the sum of x+y is 15-35.

2. A biocidal complex of claim 1 where x+y=20-25.

3. A method of controlling microorganisms in an aqueous system easily contaminated with microorganisms comprising treating said system with a biocidally effective amount of a complex of methylene bis(thiocyanate and an oxyalkylated fatty amine salt of the formula

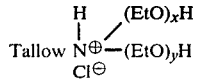

where the sum of $x+y$ is 15–35.

4. A water soluble biocidal complex of methylene bis(thiocyanate) with a salt of an ethoxylated coco amine.

5. A complex of claim 4 where said salt is a hydrochloride.

6. A complex of claim 1 wherein said salt is the hydrochloride of ethoxylated coco amine, and the weight proportion of EtO to amine is 2.5 to 1.

* * * * *